United States Patent [19]

Someya

[11] Patent Number: 5,445,824
[45] Date of Patent: Aug. 29, 1995

[54] PHYSIOLOGICAL ACTIVATING MATERIAL EXTRACTED FROM CORAL SAND

[75] Inventor: Nobuo Someya, Tokyo, Japan

[73] Assignee: Marine Bio Co., Ltd., Tokyo, Japan

[21] Appl. No.: 101,065

[22] Filed: Aug. 3, 1993

[51] Int. Cl.$^6$ ............ A61K 35/56; A61K 33.14; A61K 47/00; A61K 33/06

[52] U.S. Cl. ............ 424/520; 424/724; 424/682; 424/617; 424/630; 424/639; 424/641; 424/646; 424/667

[58] Field of Search ............ 424/520, 617, 630, 637, 424/639, 641, 646, 667, 682, 724

[56] References Cited

U.S. PATENT DOCUMENTS

| | | | |
|---|---|---|---|
| 3,890,225 | 6/1975 | Kajiyama | 210/38 |
| 4,463,031 | 7/1984 | Someya | 427/217 |
| 4,540,584 | 9/1985 | Someya | 424/156 |
| 4,781,841 | 11/1988 | Someya | 210/747 |
| 4,857,306 | 8/1989 | Roller | 424/63 |
| 5,084,337 | 1/1992 | Someya | 428/323 |
| 5,169,682 | 12/1992 | Asai | 427/217 |
| 5,187,125 | 2/1993 | Someya | 501/1 |

OTHER PUBLICATIONS

Endo et al C.A. 76: 139197g (1970) (Coral Extracted Salt Product for Food Use).
Hazama Derwent Abstr. of JPN. 03000789 (Jan. 7, 1991) (Coral Powder Dentifrice Abrasive).
Handa Derwent Abstr. of JPN 02311546 (Dec. 27, 1991) (Coral to Keep Food Fresh).

*Primary Examiner*—Shep K. Rose
*Attorney, Agent, or Firm*—Burns, Doane, Swecker & Mathis

[57] ABSTRACT

The inventor found for the first time that an extracted material from coral sand occurring in nature contains physiological activating substances. Based on this observation, in a process according to the present invention, physiological activating substances are extracted from coral sand by an appropriate extraction method. The extracted physiological activating substances are used as ingredients of cosmetics, food, and medicines. According to the present invention, physiological activating substances can be extracted in an industrially available form.

4 Claims, No Drawings

PHYSIOLOGICAL ACTIVATING MATERIAL EXTRACTED FROM CORAL SAND

BACKGROUND OF THE INVENTION

1. Technical Field

The present invention relates to a utilization art of coral sand which occurs in nature, and more particularly to physiological activating materials or substances extracted from coral sand and its utilization art.

2. Prior Art Statement

The inventor proposes that coral sand which occurs in nature be employed as a purifying agent of drinking water, a food antiseptic, and so on.

Coral sand can be obtained from a living skeleton and a fossil cluster of hermatypic coral. The coral sand, the main ingredient of which is calcium carbonate (about 95%), contains such important organism ingredients as magnesium, strontium, sodium, potassium, phosphorus, chlorine, and such essential inorganic vitamin elements as a trace amount of iron, copper, zinc, manganese, cobalt, chromium. These elements are built up and weathered by the life activity of hermatypic coral, which is a coelenterate. Accordingly, since the coral sand has an ecological chemical composition, it is a harmless material to humans, unlike materials obtained by chemical treatments.

Physiological activating substances have attracted the attention in recent years, and attempts have been made at using the physiological activity substances for a variety of purposes. As things now stand, however, no proposals have been made in an industrially available concrete way as to from where to obtain the physiological activity substances, or how to use the physiological activity substances.

The object of the present invention, taking this into consideration, lies in proposing the method for extracting physiological activating substances and the use of the extracted physiological activating substances.

DESCRIPTION OF THE INVENTION

The inventor found for the first time that physiological activating substances are present in an extracted substance or fluid from coral sand, which can be obtained in a treatment process in which washing and so on is performed to use coral sand for a variety of purposes. Such an extracted substance or fluid obtained in a treatment process was previously discarded as useless. However, finding physiological activating substances in the waste, the inventor devised to extract physiological activating substances from coral sand.

Coral sand occurs in nature and can be obtained in large quantities. Hence, according to the method of the present invention, the required amount of physiological activating substance can be obtained without fail for the first time.

The physiological activating substances thus extracted from coral sand can be employed as raw materials of cosmetics, medicines, and food, for instance. Of course, these are only a few examples of use, and they can be used in a variety of other fields.

Physiological activating substances can be extracted from coral sand as in the following way, for instance. Firstly, the extraction is performed under a fixed condition from coral sand obtained from nature, as it is, or crushed to a fixed particle size. Such extraction methods as a vacuum extraction method, a solvent extraction method, and an extraction method with heating under reduced pressure can be employed. Secondly, only physiological activating substances contained in the extracted substance are separated from the extracted substance employing an appropriate separation method.

The inventor has confirmed that coral sand contains physiological activating substances by performing a detailed component analysis of coral sand. Table I shows a component analysis of coral uncalcined calcium consisting of coral sand sold by the assignee of the present invention under the commercial name of "Coral Star". The analysis was done by a corporate juridical person Tokyoto-Shokuhin-Eisei-Kyokai at the inventor's request.

Table 2 shows the result of the analysis of the composition of amino acid composition in Table 1 after it is separated.

As is clear from these tables, it has been confirmed that coral sand contains physiological activating substances.

TABLE 1

| Title and number of the subject tested | | |
|---|---|---|
| Coral uncalcined calcium (Coral Star) | | One |
| Content and results of the test | | |
| Calcium | | 37.0% |
| Magnesium | | 1.7% |
| Sodium | | 1200 ppm |
| Potassium | | 10 ppm |
| Iron | | 1220 ppm |
| Phosphorus | | 360 ppm |
| Lipide | | 0.1% |
| Carbohydrate | | 2.2% |
| Total amount of amino acid | | 51.9/100 g |
| Silicon (SiO2) | | 2100 ppm |
| Fluorine | | 270 ppm |
| Chlorine | | 190 ppm |
| Sulfur | | 2100 ppm |
| Iodine | not detected | (10 ppm) |
| Copper | | 0.8 ppm |
| Zinc | | 2.4 ppm |
| Chromium | not detected | (2 ppm) |
| Molybdenum | not detected | (2 ppm) |
| Nickel | not detected | (1 ppm) |
| Cobalt | not detected | (1 ppm) |
| Manganese | | 12 ppm |
| Vanadium | not detected | (20 ppm) |
| Selenium | | 0.05 ppm |
| Boron | | 10 ppm |
| Bromine | | 2 ppm |

The value in the parentheses shows the inspection limit.

Concluded

TABLE 2

| Title and number of the subject tested | |
|---|---|
| Coral uncalcined calcium (Coral Star) | One |
| Content and results of the test | |
| Composition of amino acid (in 100 g) | |
| Aspartic acid | 18.1 |
| Threonine | 1.7 |
| Serine | 1.4 |
| Glutamic acid | 6.2 |
| Glycine | 4.7 |
| Cystine | 0.2 |
| Valine | 2.7 |
| Methionine | 0.7 |
| Isoleucine | 2.0 |
| Leucine | 2.6 |
| Tyrosine | 1.2 |
| Phenylalanine | 2.1 |
| Lysine | 1.3 |
| Histidine | 0.4 |
| Arginine | 1.1 |
| Proline | 2.2 |
| Tryptophane | less than 0.1 |
| Alanine | 3.3 |

As was explained above, according to the present invention, physiological activating substances or materials are extracted from coral sand occurring in large quantities in nature. Hence, only the method according to the present invention, the required amount of physiological activating substances can be obtained.

I claim:

1. In the art of extracting physiological activating substances from coral sand, the improvement which comprises the steps of:

obtaining calcium, magnesium, sodium, potassium, iron, phosphorus, lipides, carbohydrates, amino acids, silicon, fluorine, chlorine, sulfur, iodine, copper, zinc, manganese, selenium boron, and bromine according to a process selected from the group consisting of:

(a) applying a vacuum extraction method to the coral sand to separate the physiological activating substances therefrom;

(b) applying a solvent extraction method to the coral sand to separate the physiological activating substances therefrom; and (c) heating the coral sand under reduced pressure to separate the physiological activating substances therefrom.

2. The method of claim 1, wherein the obtaining process is applying a vacuum extraction method to the coral sand and separating the physiological activating substances therefrom.

3. The method of claim 1, wherein the obtaining process is applying a solvent extraction method to the coral sand to separate the physiological activating substances therefrom.

4. The method of claim 1, wherein the obtaining process is heating the coral sand under reduced pressure to separate the physiological activating substances therefrom.

* * * * *